United States Patent [19]

Raley

[11] Patent Number: 4,761,322

[45] Date of Patent: Aug. 2, 1988

[54] LAMINATED FIBROUS WEB COMPRISING DIFFERENTIALLY BONDED LAYERS, AND METHOD AND APPARATUS FOR MAKING THE SAME

[75] Inventor: John M. Raley, Appleton, Wis.

[73] Assignee: Kimberly-Clark Corporation, Neenah, Wis.

[21] Appl. No.: 785,370

[22] Filed: Oct. 7, 1985

[51] Int. Cl.$^4$ .............................................. B32B 27/14
[52] U.S. Cl. ..................................... 428/198; 156/209; 156/219; 156/220; 156/290; 156/553; 428/172; 428/218; 428/284; 428/287; 428/296; 428/297; 428/298; 428/913
[58] Field of Search ............... 428/218, 198, 284, 287, 428/170, 171, 172, 296, 298, 913; 156/209, 219, 220, 290, 553

[56] References Cited

U.S. PATENT DOCUMENTS

| | | | |
|---|---|---|---|
| 3,457,388 | 7/1969 | Lefevre | 264/103 |
| 3,480,709 | 11/1969 | Jacob et al. | 264/237 |
| 3,577,498 | 5/1971 | Matsuo et al. | 264/168 |
| 3,692,618 | 9/1972 | Dorschner et al. | 161/72 |
| 3,912,567 | 10/1975 | Schwartz | 156/167 |
| 3,920,784 | 11/1975 | Nakagawa et al. | 264/168 |
| 3,949,130 | 4/1976 | Sabee et al. | 428/192 |
| 4,013,816 | 3/1977 | Sabee et al. | 428/288 |
| 4,041,203 | 8/1977 | Brock et al. | 428/157 |
| 4,069,078 | 1/1978 | Marder et al. | 156/181 |
| 4,159,297 | 6/1979 | Mackie et al. | 264/151 |
| 4,333,979 | 6/1982 | Sciaraffa et al. | 428/179 |
| 4,340,563 | 7/1982 | Appel et al. | 264/518 |
| 4,346,052 | 8/1982 | Knox | 264/176 |
| 4,374,888 | 2/1983 | Bornslaeger | 428/198 |
| 4,377,615 | 3/1983 | Suzuki et al. | 428/213 |
| 4,405,297 | 9/1983 | Appel et al. | 425/72 |
| 4,436,780 | 3/1984 | Hotchkiss et al. | 428/198 |

Primary Examiner—James J. Bell
Attorney, Agent, or Firm—Paul Yee

[57] ABSTRACT

A laminated fibrous web comprising: a first fibrous layer; and a second fibrous layer bonded to and of lower density than the first fibrous layer; wherein fibers in the second fibrous layer are less bonded to one another, than fibers in the first fibrous layer are bonded to one another; and wherein the first and second fibrous layers are less bonded to each other than fibers in the first fibrous layer are bonded to one another. Also disclosed are a method and apparatus for making such laminated fibrous webs, by the steps of forming a first fibrous layer of a first relatively higher density; bonding fibers of the first fibrous layer to one another at a first relatively higher extent of bonding; forming a second fibrous layer at a second relatively lower density; bonding fibers in the second fibrous layer to one another at a second relatively lower extent of bonding; and bonding the first and second fibrous layers to each other at a third relatively lower extent of bonding of fibers to one another in the first fibrous layer. Apparatus is also described for carrying out such method by sequential thermal pattern-bonding of the respective web layers.

22 Claims, 3 Drawing Sheets

LAMINATED FIBROUS WEB COMPRISING DIFFERENTIALLY BONDED LAYERS, AND METHOD AND APPARATUS FOR MAKING THE SAME

BACKGROUND OF THE INVENTION

1. Field Of The Invention

This invention relates generally to fibrous web laminates suitable for use in articles such as disposable diapers, sanitary napkins, incontinence garments, and the like, and to a method and apparatus for making same. More specifically, the invention relates to a fibrous web laminate wherein a fibrous layer having a soft texture is laminated with a contiguous layer having a greater structural integrity such that the soft texture layer may be utilized as a skin-contacting surface and the contiguous layer thereto may provide mechanical strength and integrity to the laminate.

2. Description Of The Prior Art

U.S. Pat. No. 4,333,979 to M. A. Sciaraffa, et al. discloses a nonwoven web of thermoplastic fibers which is pattern bonded and further embossed to provide an increased effective thickness providing softness and bulk of the nonwoven material while retaining other desirable characteristics such as strength. The web is a spunbonded material composed of a closely-spaced point fused areas (constituting a spunbonded pattern) with the subsequently applied embossing pattern comprising much larger embossments. The resultant material is said to be highly effective as a liner for disposable products such as diapers, sanitary napkins and the like. The nonwoven web in this system is bonded by passage through a pattern nip formed by heated rolls, whereby individual compacted fused areas are formed occupying about 5 to 50% of the total web area with a density of about 50 to 3,200 fused areas per square inch. The further processing involves application of a gross embossing pattern imparting a substantially permanent deformation to the web in the form of a pattern of depressed areas. This gross pattern embossment is preferably obtained by passing the pattern-bonded web through a nip formed by a matched set of heated web embossing rolls. The gross pattern occupies an area of about 5 to 80% of the web surfaced with embossed pattern frequency in the range of from about 1 to 500 depressions per square inch. The disclosed webs have a basis weight in the range of from 0.4 ounces per square yard to 2.0 ounces per square yard, with web density being in the range of 0.08 to 0.20 gm/cc. The material of the nonwoven web includes meltspun fibers of thermoplastics such as polyolefins, polyethylene, polypropylene, polyesters, polyamides and composites thereof with cellulosic fibers. The patent describes the use of the disclosed nonwoven web as a topsheet of a diaper including a backsheet, an absorbent layer, and topsheet.

The teachings of the Sciaraffa patent relate to a doubly-embossed, single layer web. Because the web is a monolayer, the dual embossing steps will provide strengthening of the web structure, but such improvement in structural integrity is obtained at the expense of the softness and flexibility characteristics of the web stock from which the embossed product is made.

U.S. Pat. No. 4,374,888 to S. R. Bornslaeger discloses a nonwoven fabric laminate suitable for use in the manufacture of tents, outer garments, tarpaulins and the like, which comprises an outer spunbonded layer having ultraviolet radiation resistance imparted thereto, an intermediate microporous meltblown layer, preferably densified for resistance to liquid strike-through, and an inner spunbonded nonwoven layer treated for flame retardancy. The spunbonded layers preferably are formed with spotbonds, and have a basis weight of from about 0.5 to 5 ounces per square yard, with the intermediate meltblown layer having a basis weight of from about 0.5 to 2.0 ounces per square yard. Also disclosed is an embodiment wherein the spunbonded/meltblown/spunbonded laminate is pattern-bonded in a gross pattern occupying an area of 5 to 20% of the surface at a bond density of about 10 to 40 bonds per square inch. As shown in FIG. 4 of the patent, the laminate is spotbonded, and then pattern-bonded with a gross pattern of surface depressions being applied to both sides of the laminate; each layer of the laminate thus is correspondingly deformed by the gross pattern-bonding. The laminate is formed by lay-down of a spunbonded layer on a support belt, with the meltblown layer being formed directly on the spunbonded web, and a second spunbonded web then being applied to the meltblown layer to complete the composite, following which the entire composite is passed through a nip roll assembly for pattern-bonding. The laminate formed by the method of this patent suffers the same deficiency as the embossed web in the previously described Sciaraffa, et al. patent, in that the entire laminate is bonded, the spunbonded layers being dually bonded. Accordingly, the laminate by the inherent character of the pattern-bonding process has reduced flexibility and surface softness characteristics which, although not severely detrimental in the uses contemplated in the Bornslaeger patent, viz, in tents, outer garments, tarpaulins, and the like, render the laminate inadequate for the end-use application contemplated for the present invention.

U.S. Pat. No. 3,912,567 to R. J. Schwartz discloses a process for intermittent autogenous bonding of a continuous filament web. The web is passed directly through a nip formed by a smooth hard-surfaced roll and a roll containing raised points on its surface, both rolls being maintained at a temperature near the softening point of the filaments. This process is carried out such that the temperature of the web is not substantially increased before maximum pressure has been developed in the nip, but at maximum pressure is rapidly raised to effect surface fusion before a significant increase in filament crystallinity occurs. The purpose of the disclosed process is to provide two-sided surface abrasion resistance, with good physical strength properties, for high basis weight webs. The term "intermittent autogenous bonding" in this patent refers to bonding by application of heat to a substantially unbonded web at intermittent areas which define the upper and lower surfaces of intermittent regions of the web which are compressed under a pressure of at least about 2,000 psi. The process disclosed in this patent involves a two-sided monolayer web, and utilizes only one embossing step.

U.S. Pat. No. 4,069,078 to M. D. Marder, et al. discloses a finishing process for preparing nonwoven bonded sheets having high delamination strength and uniform appearance. The starting lightly consolidated sheet material is embossed by passage through a nip formed between two rolls, one of which has a multiplicity of bosses on substantially its entire surface, the bosses having a height of about 50–100% of the thickness of the sheet, with tips which have at least one dimension less than about 0.64 cm and the most prominent of which, in aggregate, form an area which is from 1–50% of the area of the surface of the roll. The resulting embossed sheet passes through a heating zone for fusion of the surface film-fibrils and then cools the sheet below its distortion temperature. Such heating/cooling steps being carried out for each of the two sides of the sheet to obtain a bonded sheet of suitable opacity. As in the previously described prior art, this patent discloses a process for a single nonwoven sheet of material, wherein a single embossing step is carried out.

U.S. Pat. No. 4,041,203 to R. J. Brock, et al. discloses a nonwoven material comprising an integrated mat of thermoplastic polymeric microfibers and a web of substantially continuous, randomly deposited, molecularly oriented filaments of the thermoplastic polymer. The microfiber mat and the continuous filament web are attached by autogenous bonding at intermittent discrete regions to utilize the continuous filament web as a load bearing constituent of the material which has desired strength characteristics and possesses a textile-like appearance, drape and hand. In manufacture, the continuous filament web is formed by laydown of spun filaments on a foraminous carrier belt and the integrated microfiber mat is brought into laminar contact with the continuous filament web to form the unbonded two-ply laminate. Subsequently, the bonding attachment between the mat and web is effected by passage of the composite laminate through a pressure nip formed between heated rolls, one of which contains a plurality of raised points on its surface. An intermittent bond pattern is preferably employed, so that the area of the web occupied by bonds after passage through the nip is about 5–50% of the surface area of the materials, the discrete bonds being present at a density of about 50–1000/in$^2$. This patent discloses a multilayered web, but the layers are bonded by only a single thermal embossing step, so that it suffers the disadvantages referred to hereinabove, viz, loss of flexibility and soft surface texture.

U.S. Pat. No. 4,436,780 to H. W. Hotchkiss, et al. discloses a nonwoven wiper laminate including a relatively high basis weight intermediate layer of meltblown thermoplastic microfibers, e.g., of polypropylene, and outer lightweight layers of generally continuous filament thermoplastic fibers, e.g., spunbonded polypropylene, having a larger average diameter. In the manufacture of the disclosed laminate, the respective layers are superpositioned relative to one another and the tri-plied composite then is passed through the nip between a patterned roll and anvil roll to pattern bond same. Again, this patent discloses a multilayer composite wherein a single embossing step is utilized for the composite.

U.S. Pat. No. 3,949,130 to R. M. Sabee, et al. discloses a spunbonded web of continuous synthetic filaments having one side that is at least two times smoother than the opposite side, wherein the majority of filament cross-points within the web are fuse-bonded to one another during the spinning of the web. The laydown of the filaments on a collection surface results in flattening on the laydown side to produce a smooth surface, the other side of the web comprising filaments which are randomly entangled to form a rough surface. Such web is disclosed to be useful in disposable diapers or like articles in which the rough side of the web faces and serves to anchor an absorbent pad, preferably also acting as a moisture carrier for wicking moisture through the web and into the absorbent pad, and the smooth side of the web provides a surface for comfortable contact with the baby's skin.

As shown in FIG. 6 of this patent, there is a steep density gradient from the smooth side to the rough side of the disclosed web, the density for the smooth side being approximately 0.32 gm/cm$^3$ and the density for the rough side being approximately 0.04 gm/cm$^3$. Thus, the smooth side of the web is of higher density which increases the difficulty of liquid penetrating into the web, in contradistinction to the rough side which is of lower density and, as mentioned in the patent's Abstract, has utility for wicking moisture through the web and into the absorbent pad. The disclosed web has texture characteristics on the respective sides which are appropriate for the intended use, i.e., a smooth side against the baby's skin and a rough side which serves to prevent shifting or displacement of the absorbent pad disposed contiguous thereto, but such textural characteristics are at odds with the function of the web in providing fast and intensive wicking action for removal of liquid from contact with the baby's skin. Accordingly, it would be appropriate if the density characteristics of the respective smooth and rough sides were reversed relative to that shown in FIG. 6, with the smooth side adjacent the baby's skin having a lower density and the rough side having a higher density thereby enhancing the anchoring action of the rough side while providing a low density, high loft fluffy baby-side surface.

U.S. Pat. No. 4,377,615 to M. Suzuki, et al. discloses a nonwoven fabric comprising an upper layer having a substantially smooth surface and a lower layer having a density lower than that of the upper layer. The upper layer comprises hydrophobic fibers as a principal element, the denier of which is finer than the denier of the lower layer, and contains a larger amount of adhesive bonding materials than the lower layer. The lower layer comprises hydrophilic fibers and hydrophobic fibers, the denier of which is coarser than the denier of the upper layer, and contains a smaller amount of adhesive bonding materials than the upper layer.

The Suzuki, et al. patent states that the upper and lower layers do not indicate a state wherein the thickness of the nonwoven fabric is equally divided into two but rather a case wherein a state of a plurality of fibrous webs formed through mixing of different fibers are overlapped to constitute a nonwoven fabric. The nonwoven fabric in such case is divided into an upper layer having a relatively higher density and a lower layer having a relatively lower density, density referring to the amount of fibers and adhesive bonding materials in each of the upper and lower layers, being averaged. The patent discloses to use fibers of polyester, polypropylene, acrylic, rayon, acetate and the like for each of the respective layers. The adhesive bonding materials described in this patent include those comprising as a main component acrylic ester copolymers, consisting of monomers such as ethylacrylate, methylacrylate and/or butylacrylate, wherein ethylacrylate is a major component.

In the manufacture of the nonwoven fabric disclosed in the Suzuki, et al. patent, the fibers for the respective layers are prepared, formed into webs and piled up by a plurality of cards. The resulting web then is guided to a saturator, where the web is dipped in a low-solids binder emulsion. The amount of binder applied to the lower layer by the saturator is comparatively small with respect to the upper layer, which downstream of the dip zone is sprayed with a higher-solids binder emulsion, whereby the upper layer has a greater binder content than the lower layer. Subsequently, the web is passed through serial driers, and then guided into contact of its upper higher density layer with a smooth-surfaced cylinder, where the web is forcibly pressed against the cylinder's surface by a plurality of rolls, to cure the web and provide a substantially smooth surface on its upper surface.

In the specification of the Suzuki, et al. patent, at column 5, line 45 to column 6, line 21 thereof, the preparation of various sample webs according to the disclosed invention are described, wherein the respective layers are formed and "these webs are piled." There is no disclosure of any type of bonding of respective layers in the web to one another, contrariwise, the webs are merely piled relative to one another, so that there is only a mechanical entanglement of fibers therebetween at the interface of the two layers. Although a bonding medium subsequently is applied to the respective top and bottom surfaces of the composite web, it would be expected that consistent with the teachings of the patent, there is no flow-through or penetration from one layer to another, since same would destroy the density gradation which is stated to be an object of the fibrous web according to the patent, i.e., each of the respective layers having its own specific density as associated with the extent of the bonding medium applied thereto. Thus, the interface will be defined by a comparatively loose assemblage of fibers which have a low level of structural integrity relative to one another so that constituent layers of the web may shift relative to one another in use. Further, the fibrous web described by this patent has a significant deficiency in that a substantially smooth surface is provided on the outer surface of the higher-density, more extensively bonded layer. Accordingly, the smooth surface in operation will function to oppose wicking or penetration of liquid through the laminated web to the contiguously positioned absorbent pad (disposed against its smooth surface). In other words, while the fluffy back surface of the fibrous web of this patent is effective to sorb fluid from a baby's skin, there is presented to such sorbed fluid a transmission barrier in the form of the substantially smooth surface positioned between such fibrous web and the absorbent pad.

SUMMARY OF THE INVENTION

In one aspect, the invention relates to a laminated fibrous web comprising:
a first fibrous layer; and
a second fibrous layer bonded to and of lower density than the first fibrous layer;
wherein fibers in the second fibrous layer are less bonded to one another than fibers in the first fibrous layer are bonded to one another; and
wherein the first and second fibrous layers are less bonded to each other than fibers in the first fibrous layer are bonded to one another.

In another aspect, the invention relates to a process for making a laminated fibrous web including:
a first fibrous layer; and
a second fibrous layer bonded to and of lower density than the first fibrous layer;
wherein fibers in the second fibrous layer are less bonded to one another than fibers in the first fibrous layer are bonded to one another; and
wherein the first and second fibrous layers are less bonded to each other than fibers in the first fibrous layer are bonded to one another,
said process comprising the steps of:
forming a first fibrous layer of a first relatively higher density;
bonding fibers of the first fibrous layer to one another at a first relatively higher extent of bonding;
forming a second fibrous layer at a second relatively lower density;
bonding fibers in the second fibrous layer to one another at a second relatively lower extent of bonding; and
bonding the first and second fibrous layers to each other at a third relatively lower extent of bonding, which is less than the first relatively higher extent of bonding of fibers to one another in the first fibrous layer.

In another aspect, the invention relates to an apparatus for forming a laminated fibrous web, comprising:
means for forming a first fibrous layer;
a first pattern-bonding means for translating the first fibrous layer in relation to the first pattern-bonding means to form thereon a first bonding pattern;
means for forming a second fibrous layer;
a second pattern-bonding means; and
means for mating the first fibrous layer after pattern-bonding thereof by the first pattern-bonding means to the second fibrous layer, with the second fibrous layer overlying said first fibrous layer to form a laminated fibrous web and translating same in contact with the second pattern-bonding means for pattern-bonding of the second fibrous layer such that the fibers of the second fibrous layer are pattern-bonded to one another and so that the second fibrous layer is pattern-bonded to the first fibrous layer;
wherein the pattern-bonding area provided by the second pattern-bonding means is lower than the pattern-bonding area provided by first pattern-bonding means.

In yet another aspect, the invention relates to apparatus for forming a laminated fibrous web, comprising:
means for forming a first fibrous layer;
a first pattern-bonding roll having on its surface an array of protrusions spaced-apart from one another to define a pattern-bonding area constituted by the areal extent of the protrusions;
means for heating the first pattern roll;
means for rotating the first pattern roll;
means for translating the first fibrous layer in contact with the first pattern roll during rotation and heating thereof to form thereon a first bonding pattern;
means for forming a second fibrous layer;
a second pattern roll having on its surface an array of protrusions spaced-apart from one another to define a pattern-bonding area measured by the areal extent of the protrusions on the second pattern roll;
means for rotating the second pattern roll;
means for heating the second pattern roll;
means for mating the first fibrous layer after pattern-bonding thereof by the first pattern roll to the second fibrous layer, with the second fibrous layer overlying the first fibrous layer to form a laminated fibrous web and translating same in contact with the second pattern roll during rotation and heating thereof for pattern-bonding of the second fibrous layer such that the fibers of the second fibrous layer are pattern-bonded to one another and such that the second fibrous layer is pattern-bonded to the first fibrous layer;

wherein the pattern-bonding area of the second pattern roll is lower than the pattern-bonding area of the first pattern roll.

As used herein, the phrase "less bonded to one another", in reference to fibers in a given layer or to the interface between respective layers of the fibrous web, means that such layer or interface contains a lower proportion of bonded fibers (i.e., bonded fibers as compared to non-bonded fibers) than the fibrous layer to which such layer or interface is compared.

BRIEF DESCRIPTION OF THE DRAWINGS

The invention will be more fully understood and further advantages will become apparent when reference is made to the following detailed description of the invention and to the drawings in which.

DETAILED DESCRIPTION OF THE PREFERRED EMBODIMENTS

Generally, the materials of the invention provide a laminated fibrous web wherein one of the fibrous web laminae is sufficiently pattern-bonded to provide high structural integrity without loss of flexibility or good surface softness of such layer, in a composite wherein a second layer is bonded to such layer in a manner providing a strong bond therebetween, but wherein the bonding does not destroy the aforementioned desired characteristics of flexibility and soft surface texture. The laminated fibrous webs of the invention may usefully be employed in absorbent articles such as disposable diapers, sanitary napkins, incontinence undergarments and the like. Other attributes and advantages of the present invention will be apparent from the ensuing disclosure and appended claims.

Figure 1:
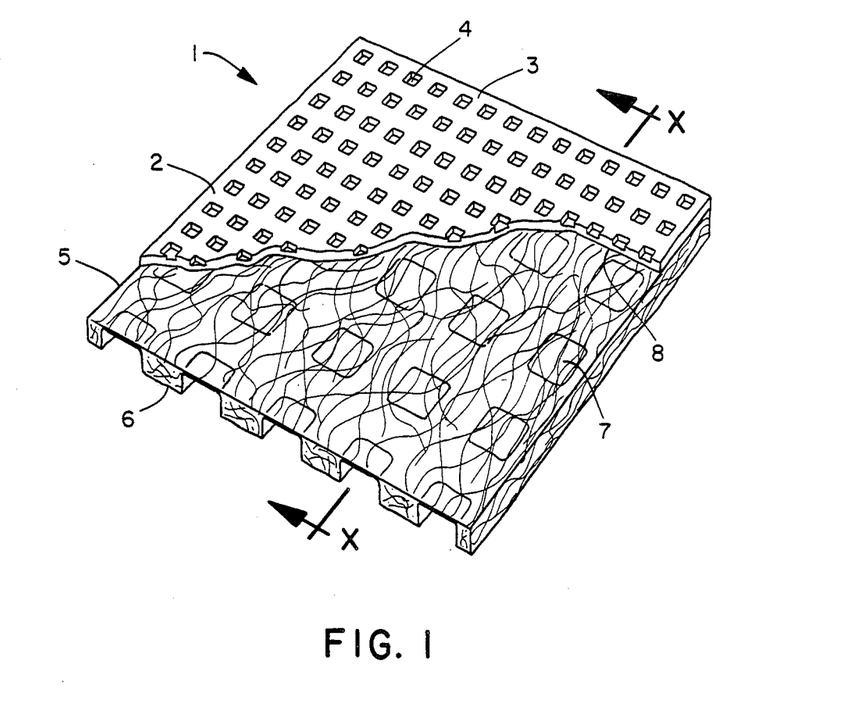
FIG. 1 is a perspective partial sectional view of a laminated fibrous web according to the present invention.

Referring now to FIG. 1, there is shown a perspective partial sectional view of a representative laminated fibrous web according to the present invention. The laminated fibrous web 1 comprises a first fibrous layer 2, through the outer surface 3 of which is formed a plurality of bonds 4 in a repeating pattern. In the shown embodiment, the bonds 4 do not extend to the interface 8 between second layer 5 and first layer 2, but end at an intermediate depth within first layer 2, short of interface 8. The first fibrous layer 2 is bonded at interface 8 to a second fibrous layer 5 through the outer surface 6 of which is disposed a plurality of bonds 7 in a repeating pattern, the bonds 7 extending through the thickness of the second layer to bond the second layer 5 to the first layer 2 at the interface 8 therebetween.

The respective first and second fibrous layers 2 and 5 may be formed of any suitable natural or synthetic fibers (filaments) in any appropriate structure, but it is preferred that these fibers be formed into nonwoven layers. Useful fibers for the respective layers include cotton, wood pulp, jute, asbestos, wool, silk, glass, fiberglass, carbon, natural fibers generally, as well as rayon, polyester, nylon, Nomex, Kevlar, acrylics, polypropylene, polyethylene, aluminum silicate and the like. The fibers may have any suitable morphology, and may include hollow or core fibers, shaped fibers, bicomponent fibers or high absorbent particle impregnated fibers, e.g., superabsorbent batts. The respective layers may comprise webs formed by any suitable procedure, for example, nonwoven webs may be made by air-laying, wet-laying, dry-laying, meltblowing, spinning, extrusion, etc. In the preferred practice of the present invention, the respective first and second fibrous layers 2 and 5, are spun-bonded materials and are comprised of thermoplastic polymer fibers, such as polypropylene, polyethylene, polyamides, polyesters such as polyethylene terephthalate, and thermoplastic elastomers such as polyurethanes.

In keeping with the present invention, the fibrous layers can be prepared in a wide variety of basis weights and fiber sizes, with the particular basis weight of a given material being selected as appropriate for the intended end-use application.

In a particularly preferred application of the present invention, wherein the laminated fibrous web is employed as a liner layer for an absorbent article, such as a diaper, sanitary napkin, incontinence brief, and the like, the first fibrous layer 2 may be formed of a material, such as polyethylene, polypropylene, polyester, polyurethane, or blends thereof, having a density of from about 0.02–0.20 gm/cc, and a basis weight of 0.2–2.0 oz/yd$^2$ (6.84–68.4 gm/m$^2$). In such preferred end-use application, the second fibrous layer 5 may be formed of fibers of polyethylene, polypropylene, polyester, polyurethane, or blends thereof having a density of from about 0.01–0.10 gm/cc and a basis weight of from about 0.2–2.0 oz/yd$^2$ (6.84–68.4 gm/m$^2$) and the ratio of the density of the first fibrous layer to the density of the second fibrous layer is not more than about 20:1 and is at least about 1:1.

Figure 2:
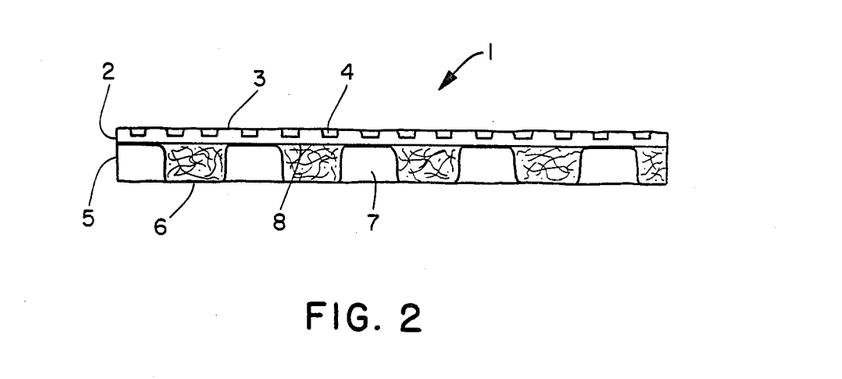
FIG. 2 is a cross-sectional elevational view of the laminated fibrous web of FIG. 1, taken along line X—X of FIG. 1.

As shown to best advantage in FIG. 2 and as described above, the laminated fibrous web 1 comprises a first fibrous layer 2 which has a series of bonds 4 in a pattern thereon, extending from the outer surface 3 of such layer into the interior of the layer but stopping short of interface 8. The bonds 4 thus take the form of a thermally produced pattern of bond sites which are formed in a manner as described hereinafter. The second fibrous layer 5 likewise has a pattern of bonds 7 extending from its outer surface 6 and into the interior thereof. In contrast to the bonds 4 of the first layer 2, however, the pattern bonds 7 extend through the entire thickness of the second fibrous layer 5 to the interface 8 between the first and second fibrous layers, to thereby effect bonding of fibers within the second fibrous layer 5 to one another, and concurrently to effect bonding of the second fibrous layer 5 to the first fibrous layer 2 at the interface 8. In the first layer 2, the pattern of bonds 4 bond the fibers in the first layer only to one another and do not bond fibrous layer 2 to fibrous layer 5.

Although bonds 4 and 7 in the respective first and second layers 2 and 5, respectively, have been described as thermally produced, it is within the purview of the present invention to utilize any suitable method of bonding the fibers in the respective layers to one another and to bond the respective first and second fibrous layers to one another at the interface therebetween. For example, the fibers in the respective first and second fibrous layers could be adhesively bonded to one another such as by pattern application of a suitable bonding medium such as an epoxy resin-based adhesive, with the fibers in the second fibrous layer 5 likewise being bonded to one another by pattern adhesive bonding, and the respective layers being bonded to each other at the interface therebetween by the same or a different bonding medium. Alternatively, the bonding of fibers to one another in each of the first and second fibrous layers could be effected by needling and the first and second layers may be joined to one another by needling as well. Thermal bonding as referred to herein includes the use of heated embossing rolls and ultrasonic bonding.

The present invention also contemplates the respective bonding of the layers in various sequences. For example, first layer 2 may be formed and bonded in a first operation, and second layer 5 may be formed and bonded in a separate operation. Then the first and second bonded layers can be bonded to each other in still another separate operation. Alternatively, in a more preferred sequence, first layer 2 is formed and bonded with bonds 4 in a first operation, and the second layer is formed onto the first layer. Then, bonds 7 are formed in layer 5 during an operation which simultaneously bonds the two layers 2 and 5 together.

As a further alternative, one or both of the first and second fibrous layers 2 and 5 may comprise bicomponent fibers having a lower melting point outer portion and a higher melting point inner core portion, wherein the bicomponent fibers are meltbonded to one another by thermally fused outer portions of contiguous zones of the bicomponent fibers. Fibers of respective lower melting point and higher melting point polyester are suitable for such purpose, and such fibers may be made in any suitable manner as known to those skilled in the art.

In the preferred practice of the invention, as mentioned hereinabove, the first and second fibrous layers will comprise thermoplastic fibers, such as those selected from the group consisting of polypropylene, polyethylene, polyester, polyurethane, and nylon, where the fibers in each of the respective first and second layers are thermally pattern-bonded to one another and the first and second layers likewise are pattern-bonded to one another.

In application to a laminated fibrous web as shown in FIGS. 1-2, the respective layers may be bonded internally and bonded together by thermal bonding in a manner hereinafter described in greater detail.

It is a feature of the present invention that the second fibrous layer is of lower density than the first fibrous layer. It is also a feature of the present invention that the fibers in the second fibrous layer are less bonded to one another, than fibers in the first fibrous layer are bonded to one another. In such manner, the first fibrous layer having a higher density and greater extent of bonding relative to the second fibrous layer, provides a base substrate for the second layer which is characterized by greater structural integrity and mechanical strength than the second fibrous layer. Concomitantly, it is a feature of the present invention that the first and second fibrous layers are less bonded to each other than fibers in the first layer are bonded to one another, i.e., there is a greater extent of bonding in the first fibrous layer than there is between layers at the interface therebetween.

Preferably, as shown in FIGS. 1-2, the extent of bonding in the second fibrous layer is substantially the same as the extent of bonding at the interface between the first and second fibrous layers.

The various extents of bonding may be controlled in the thermal pattern-bonding of the respective layers and resulting web, as shown in FIGS. 1 and 2, so that the pattern-bonding of the first fibrous layer is characterized by a higher percent bond area than that of the second fibrous layer, and the pattern-bonding of the first fibrous layer to the second fibrous layer is characterized by a lower percent bond area than that of the first fibrous layer. As used herein, the term "percent bond area" refers to the surface area of the respective fibrous layers or interface therebetween which is occupied by bonds when pattern-bonding is employed. Thus, as shown in FIG. 1, the first fibrous layer 2 has a regular array of thermal pattern bonds 4 disposed across its outer surface 3 and the ratio of the surface area occupied by the bonds 4 to the total area of surface 3 is the percent bond area for the first fibrous layer 2. The second fibrous layer percent bond area and the interface (first-to-second fibrous layer bond) is measured analogously.

Figure 3:
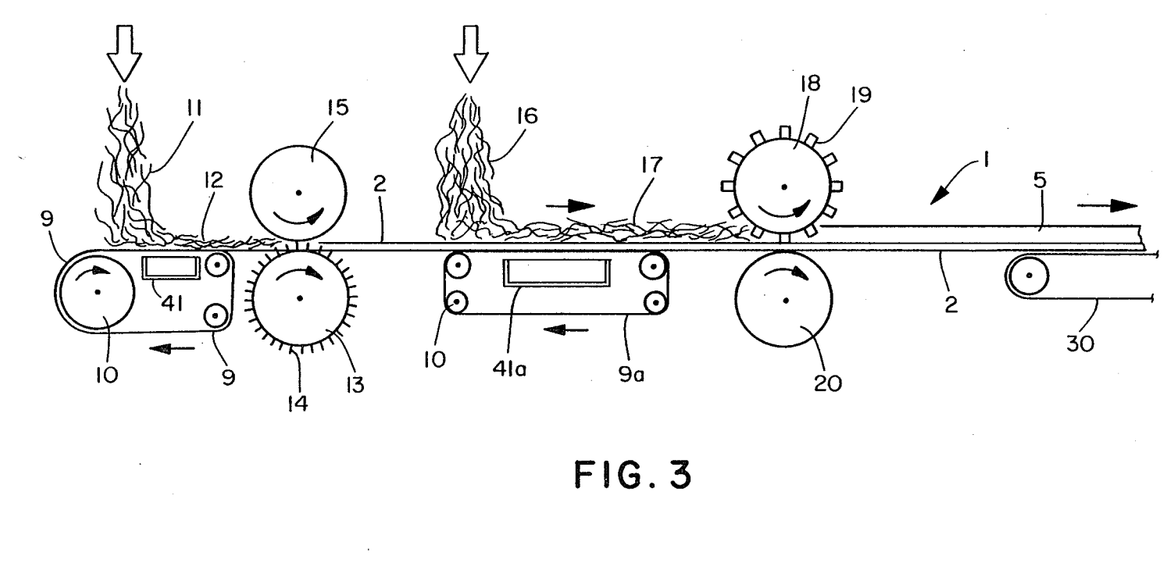
FIG. 3 is a schematic diagram of a process system according to the present invention for forming a laminated fibrous web of the type shown in FIGS. 1 and 2.

In practice, the process system schematically illustrated in FIG. 3 may utilize a multibank spunbond machine to produce the laminated, composite fibrous web 1. A base substrate layer would be formed by the first one or more banks of such multibank spunbond machine to produce the stronger first fibrous layer 2 of the composite. The remaining spinning banks of the spunbond machine would form the soft, lower density second fibrous layer 5 on top of the first fibrous layer. The second fibrous web 5 for such application is thermal bonded to first layer 2 at a very low percent bond area in order to preserve the low density, and loft of the filaments therein. The fuzziness and loft of the upper, second fibrous web can be enhanced by brushing or other mechanical treatment, as per se known in the art. The composite fibrous web 1 thus has a large degree of compressibility or "cushiness" from the low density, lofty, upper fibrous web. The length of the filaments produced by the forming means for the spun fibers may be adjusted as necessary and/or desirable in a given end use to enhance the velvet-like texture of the upper fibrous web. Preferably, when relatively short, discontinuous filaments are employed, the filaments are meltblown fibers.

The system representatively shown in FIG. 3 comprises foraminous forming surfaces 9 and 9a which are translated in the directions shown by the arrows by rollers 10. The respective rolls are joined by any suitable means to electric motors or other drive apparatus (not shown) whereby rotation of the respective rolls (in the direction shown by the arrows superimposed thereon) is effected. The foraminous forming surface 9 receives thereon a stream 11 of first fibers which deposit on the forming surface to form a web 12 of such fibers. The fibers may be deposited by gravity, or may be air-laid or fluid-laid, or may be laid on the surface under the influence of a negative pressure gradient, as for example may be provided by the disposition of a vacuum suction means, e.g., a vacuum box 41 under the foraminous forming surface 9 in the vicinity of the fibers stream, as is well known in the art.

The web 12 of first fibers then is directed by the moving forming surface 9 through a nip formed by the pair of rolls 13, 15. Roll 13 as shown comprises a pattern roll which is provided with an array of protrusions 14 on its surface, the protrusions being spaced apart from one another to define a bonding area constituted by the areal extent of the protrusions. As used herein, the term "areal extent of the protrusions" refers to the area defined by the extremities of the protrusions which, during rotation of the roll 13 contact the web and provide thermal fusing of the fibers to form a series of pattern bonds of depression-like shapes in the surface of the first fibrous layer, extending into the interior thereof as shown in FIG. 2. The first pattern roll 13 is heated (by means not shown), whereby the extremities of the protrusions are at approximately the softening point of the thermoplastic fibers of the web. Roll 15 is a smooth-surfaced roll which functions as an anvil roll relative to the pattern roll 13.

After passage through the nip defined by the rolls 13, 15 the first fibrous layer 2 having thermal pattern bonds 4 thereon (FIG. 2) is passed by the forming surface 9a to a second fiber deposition zone, where a stream 16 of second fibers, which may be spunbonded or meltblown fibers, is deposited on the first fibrous layer 2 to form a nonwoven web 17 thereon. A vacuum box 41a can be employed to help deposit these second fibers. The resulting bi-layer web passes through a nip defined by the pair of rolls 18 and 20, 18 comprising a pattern roll. The second pattern roll 18 is a bonding roll having on its outer surface an array of protrusions 19 spaced-apart from one another to define a pattern-bonding area measured by the areal extent of the protrusions. The pattern roll is opposedly positioned relative to the smooth-surfaced roll 20, whereby the latter functions as an anvil roll vis-a-vis the former. In the same manner as previously described for the first pattern roll 13, the second pattern roll 18 is heated (by means not shown) so that the extremities of the protrusions 19 are at a temperature which is at approximately the softening point of the fibers constituting the web 17 of second fibers. The bi-layer web, comprising web 17 of the second fibers passes through the nip defined by the second pattern roll 18 and smooth-surfaced roll 20 to form a series of thermal pattern bonds 7 thereon as shown in FIG. 2, wherein the pattern bonds extend into the interior of the second fibrous layer 5 to the interface 8 between the respective first and second layers, thereby concurrently thermally bonding the first fibrous layer 2 to second fibrous layer 5. The resulting laminated fibrous web 1, comprising the internally bonded first fibrous layer 2 interbonded to the internally bonded second fibrous layer 5, is conveyed by transporting means 30 to end-use processing steps, which may include mating of the laminated fibrous web 1 with absorbent sheets and moisture-impervious sheets to form a multiple layer absorbent article suitable for use as disposable diapers, sanitary napkins and the like.

It will be recognized that the laminated fibrous web 1, which is shown in FIGS. 1 and 2, is positioned in those drawings in an inverted, reverse fashion to the fibrous web 1 as shown in FIG. 3 exiting from the nip defined by rolls 18 and 20, respectively. Thus, in FIG. 3 the first fibrous layer 2 after pattern-bonding thereof by the first pattern roll 13 is mated to the precursor web 17 of the second fibrous layer 5, with web 17 overlying the first fibrous layer 2, to form a laminated fibrous web. The resulting laminated fibrous web is translated in contact with the second pattern roll 18 during rotation thereof for pattern-bonding of web 17 to produce second fibrous layer 5. During this processing operation the fibers of second fibrous layer 5 are pattern-bonded to one another, and the second fibrous layer is pattern-bonded to the first fibrous layer 2. As indicated, the pattern-bonding area provided by the second pattern roll 18 is less than the pattern-bonding area provided by the first pattern roll 13, as shown in FIG. 3 by the difference in size and number of the respective protrusions on the first and second pattern rolls 13 and 18, respectively. Consequently, the proportional amount of bonded area within layer 2 is greater than the proportion of the bonded area in the lesser bonded layer 5. This results in a relatively higher strength in the more bonded layer 2, and results in a relatively greater softness within the lesser bonded layer 5. Optionally, layer 5 may be brushed to further increase its loft and softness.

In the practice of the invention wherein the laminated fibrous web 1 is used as a liner for garments, such as disposable diapers, sanitary napkins, incontinence garments or similar articles, the ratio of the lower pattern-bonding area of the second pattern roll 18 to the greater pattern-bonding area of the first pattern roll 13 is at least about 1:10 but is less than 1:1. In such application, the less bonded layer preferably is the skin-contacting layer in the article, due to the fact that its lower bonding extent provides a softer, more flexible surface which is better compatible with the user's skin than is the more bonded layer. It will be appreciated however, that the utility of the invention is extremely varied, and that the ratio of bonding area of the second roll to the bonding area of the first roll may be varied within wide limits depending on the end usage of the laminated fibrous web produced thereby, and the desired strength, integrity and softness characteristics of the respective fibrous layers.

Figure 4:
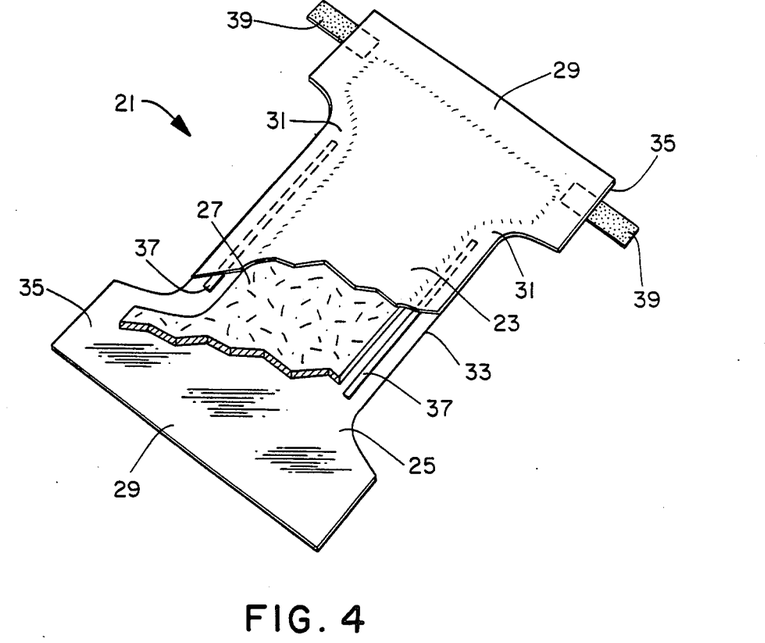
FIG. 4 representatively shows a disposable diaper which incorporates a liner comprised of the laminated fibrous web of the invention.
Figure 5:
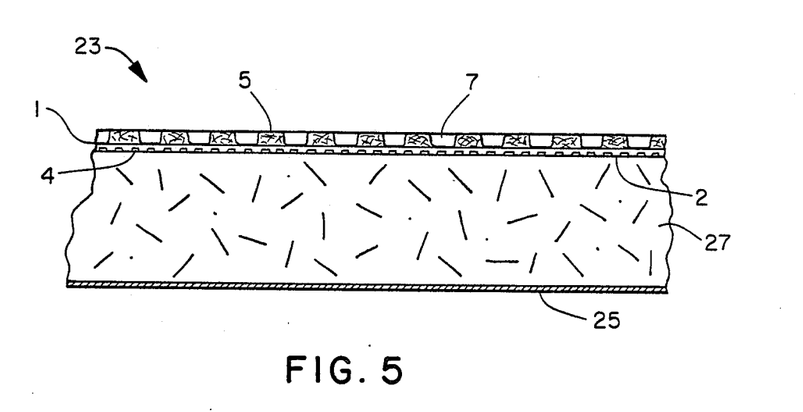
FIG. 5 representatively shows a cross sectional view of the arrangement of the laminated web liner within the diaper illustrated in FIG. 4.

FIGS. 4 and 5 illustrate an example of an article incorporating the laminated web of the invention. Disposable diaper 21 comprises a liquid-permeable inner liner 23, a liquid-impermeable outer layer 25, and an absorbent batt 27 secured therebetween. The inner liner 23 and outer layer 25 are larger than the absorbent batt 27, have end marginal portions 29 extending beyond the ends of the batt and have side marginal portions 31 extending beyond the sides of the batt. The liner 23 and outer layer 25 are secured to each other along the marginal portions 29 and 31.

The inner liner 23 may be any soft, flexible porous sheet which passes fluids therethrough, and preferably comprises a nonwoven fibrous web or sheet such as the differentially bonded web laminate of the present invention. Optionally, the liner may be treated with a surfactant to aid in liquid transfer.

The outer layer 25 is a liquid-impermeable layer and may comprise a thin web or sheet of plastic film such as polyethylene, polypropylene, polyvinyl chloride or the like. It may be transparent or have an embossed or matte surface to be opaque.

The absorbent batt 27 may be of any suitable absorbent material. Typically, the batt is composed of a cellulosic material, such as an airformed layer of wood pulp fibers commonly known as "fluff."

The inner liner 23, outer layer 25 and batt 27 may be combined with one another in any suitable manner to form the finished diaper. The elements may be bonded to one another by means of strips or patterns of hot melt or pressure sensitive adhesive, overall or patterned heat sealing, strips of double faced pressure sensitive adhesive tape, etc. A particularly effective bonding system is the use of spaced parallel lines of hot melt adhesive on the interior surface of the outer layer 25, with the absorbent batt bonded to the layer 25 along sections of the lines of adhesive and the inner liner 23 bonded to the layer 25 along other sections of the lines of adhesive within the marginal portions 29 and 31 outside the batt.

The diaper is of a generally "hourglass" or I-shape including a central narrowed crotch section 33 and waistband sections 35 along each end thereof. Elongate elastic means 37 are secured in place adjacent the absorbent batt 27 on each side thereof to develop gathered elastic leg portions that are conformable with an infant's legs. Conventional pressure-sensitive tapes 39 are attached to one waistband section 35. The diaper 21 is fitted to an infant with the inner layer 23 against the child's skin; one marginal portion 29 encircles part of the infant's waist and the other marginal portion 29 encircles the balance, with the two being overlapped and joined together by the pressure sensitive adhesive tapes 39 in order to hold the diaper in place.

As representatively shown in FIG. 5, liner 23 can be comprised of differentially bonded web laminate 1. Laminated web 1 is arranged with the less bonded layer 5 facing the body of the wearer and with the greater bonded layer 2 facing the absorbent batt 27. This configuration contacts the skin of the wearer with the softer, more flexible side of laminated web 1. Alternatively, laminated web 1 can be arranged with the greater bonded layer 2 facing the body of the wearer and with the less bonded layer 5 facing absorbent batt 27. This configuration could provide an increased separation between the bodyside of laminated web 1 and absorbent batt 27, and can still provide a "cushiony" feel to the laminated web liner.

The following examples are provided to give a more detailed understanding of the invention. The particular compositions, proportions, materials and parameters are exemplary and are not intended to specifically limit the scope of the invention.

EXAMPLE 1

A first fibrous layer was formed by laying bilobal (dog-bone) cross-section filaments onto a foraminous forming surface. The filaments were composed of polypropylene and were spunbond employing conventional techniques to form a fibrous layer. This first fibrous layer had a basis weight of 0.5 oz/yd$^2$ (17.1 gm/m$^2$), and was thermobonded on one side thereof employing a patterned bonding roll. The thermal bonding was performed at a temperature of 270° F. to produce a 22–25% bond area arranged in a pattern of round, hexagonal and triangular shaped bonds.

A second fibrous layer comprised of round cross-section filaments was formed onto the first fibrous layer employing the spunbond technique. The second fibrous layer had a basis weight of 0.5 oz/yd$^2$ (17.1 gm/m$^2$), and was thermobonded with a patterned bonding roll. The thermobonding of the second fibrous layer bonded the fibers therein to one another and also bonded the second fibrous layer to the first fibrous layer. This second thermobonding procedure was performed at a temperature of 260° F. and produced a 3% bond area pattern.

The resultant composite web had the properties set forth in Table 1 below.

TABLE 1

| Basis Weight | 1.04 oz/yd$^2$ | (35.57 g/m$^2$) |
| --- | --- | --- |
| Grab Tensile, MD | 9.3 lbs. | (4.2 kg) |
| CD | 3.3 lbs. | (1.5 kg) |

TABLE 1-continued

| Ames Bulk | 0.173 inches | (4.39 mm) |
| --- | --- | --- |

MD = Machine direction
CD = Cross direction

EXAMPLE 2

A first fibrous layer was formed by laying bilobal (dog-bone) cross-section filaments onto a foraminous forming surface. The filaments were composed of polypropylene and were spunbond employing conventional techniques to form a fibrous layer. This first fibrous layer had a basis weight of 0.5 oz/yd$^2$ (17.1 gm/m$^2$), and was thermobonded on one side thereof employing a patterned bonding roll. The thermal bonding was performed at a temperature of 270° F. to produce a 22–25% bond area arranged in a pattern of round, hexagonal and triangular shaped bonds.

A second fibrous layer comprised of round cross-section filaments was formed onto the first fibrous layer employing the spunbond technique. The second fibrous layer had a basis weight of 0.8 oz/yd$^2$ (27.4 gm/m$^2$), and was thermobonded with a patterned bonding roll. The thermobonding of the second fibrous layer bonded the fibers therein to one another and also bonded the second fibrous layer to the first fibrous layer. This second thermobonding procedure was performed at a temperature of 260° F. and produced a 3% bond area pattern.

The resultant composite web had the properties set forth in Table 2 below.

TABLE 2

| Basis Weight | 1.36 oz/yd$^2$ | (46.51 g/m$^2$) |
| --- | --- | --- |
| Grab Tensile, MD | 9.3 lbs. | (4.2 kg) |
| CD | 4.1 lbs. | (1.9 kg) |
| Ames Bulk | 0.250 inches | (6.35 mm) |

EXAMPLE 3

A first fibrous layer was formed by laying bilobal (dog-bone) cross-section filaments onto a foraminous forming surface. The filaments were composed of polypropylene and were spunbond employing conventional techniques to form a fibrous layer. This first fibrous layer had a basis weight of 0.6 oz/yd$^2$ (20.5 gm/m$^2$), and was thermobonded on one side thereof employing a patterned bonding roll. The thermal bonding was performed at a temperature of 260° F. to produce a 22–25% bond area arranged in a pattern of round, hexagonal and triangular shaped bonds.

A second fibrous layer comprised of round cross-section filaments was formed onto the first fibrous layer employing the spunbond technique. The second fibrous layer had a basis weight of 1.0 oz/yd$^2$ (34.2 gm/m$^2$), and was thermobonded with a patterned bonding roll. The thermobonding of the second fibrous layer bonded the fibers therein to one another and also bonded the second fibrous layer to the first fibrous layer. This second thermobonding procedure was performed at a temperature of 280° F. and produced a 3% bond area pattern.

The resultant composite web had the properties set forth in Table 3 below.

TABLE 3

| Basis Weight | 1.87 | (63.96 g/m$^2$) |
| --- | --- | --- |
| Grab Tensile, MD | 13.3 lbs. | (6.0 kg) |
| CD | 6.6 lbs. | (3.0 kg) |

TABLE 3-continued

| Ames Bulk | 0.293 inches | (7.44 mm) |

EXAMPLE 4

A first fibrous layer was formed by laying bilobal (dog-bone) cross-section filaments onto a foraminous forming surface. The filaments were composed of polypropylene and were spunbond employing conventional techniques to form a fibrous layer. This first fibrous layer had a basis weight of 0.4 oz/yd$^2$ (13.7 gm/m$^2$), and was thermobonded on one side thereof employing a patterned bonding roll. The thermal bonding was performed at a temperature of 280° F. to produce a 22–25% bond area arranged in a pattern of round, hexagonal and triangular shaped bonds.

A second fibrous layer comprised of round cross-section filaments was formed onto the first fibrous layer employing the spunbond technique. The second fibrous layer had a basis weight of 0.8 oz/yd$^2$ (27.4 gm/m$^2$), and was thermobonded with a patterned bonding roll. The thermobonding of the second fibrous layer bonded the fibers therein to one another and also bonded the second fibrous layer to the first fibrous layer. This second thermobonding procedure was performed at a temperature of 280° F. and produced a 3% bond area pattern.

The resultant composite web had the properties set forth in Table 4 below.

TABLE 4

| Basis Weight | 1.34 oz/yd$^2$ | (45.83 g/m$^2$) |
| Grab Tensile, MD | 9.1 lbs. | (4.1 kg) |
| CD | 4.6 lbs. | (2.1 kg) |
| Ames Bulk | 0.238 inches | (6.05 mm) |

The Ames bulk data set forth in the above examples were derived employing an Ames thickness (bulk) tester Model 3223 (or equivalent) available from B.C. Ames Company, Waltham, Mass. The tester was equipped with a long range dial indicator, 0–100 dial units with 0.001" graduation, having a full span of 3.0 inches. The compression spring was removed as well as the raising and lowering arm. A J50B Universal joint (available from Wisconsin Bearing Company, Appleton, Wisc.) was fabricated and attached to the bottom of the vertical weight attachment rod, and to the top of a 5"×5" platen. The total weight of the platen, weight attachment rod, and added weights was 0.4 lbs.±0.01 lbs. (182±5 grams).

Ten 4"×4" samples were cut making certain that there were no folds, creases, wrinkles, etc. in the sample selected. The 10 samples were stacked on top of each other with the MD of each sample aligned in the same direction. The platen was raised sufficiently to place the stack of ten 4"×4" samples on the bed plate, centered under the 5"×5" platen as much as possible. The platen was then gently released onto the material, and a reading was taken 15–20 seconds after the platen was released on the material. The bulk or thickness was measured to the nearest 0.001 inch.

Although preferred embodiments of the invention have been described in detail, it will be appreciated that numerous variants, modifications and other embodiments are possible, and all such apparent variants, modifications and embodiments are to be regarded as being within the spirit and scope of the present invention.

What is claimed is:

1. A laminated fibrous web, comprising:
    a first fibrous layer, which has fibers thereof bonded to one another with a first, spaced-apart bonding pattern having a first bonding area, and which has a first density, as determined prior to said bonding thereof; and
    a second fibrous layer, which is composed of fibers bonded to one another with a second, spaced-apart bonding pattern having a second bonding area which is less than said first pattern bonding area, said second fibrous layer having a second density, as determined prior to said bonding thereof, which is less than said first fibrous layer density;
    wherein said second bonding pattern produces bonds between said first and second fibrous layers, and said first bonding pattern does not produce bonds between said first and second fibrous layers.

2. A laminated fibrous web as recited in claim 1, wherein said first and second fibrous webs comprise nonwoven webs.

3. A laminated fibrous web as recited in claim 2, wherein said first bonding pattern provides a first series of bonds which extend into said first fibrous layer but stop short of an interface between said first and second fibrous layers, and wherein said second bonding pattern provides a second series of bonds which extend entirely through said second fibrous layer to said interface.

4. A laminated fibrous web according to claim 2, wherein the first and second fibrous layers each comprise spunbonded webs.

5. A laminated fibrous web according to claim 2, wherein fibers in each of the first and second fibrous layers are thermally bonded to one another and the first and second fibrous layers are thermally bonded to one another.

6. A laminated fibrous web according to claim 2, wherein the density of the first fibrous layer is about 0.02 to 0.2 gm/cc, the density of the second fibrous layer is about 0.01 to 0.1 gm/cc, and the ratio of density of the first fibrous layer to the density of the second fibrous layer is about 20:1 to 1:1.

7. A laminated fibrous web according to claim 2, wherein at least one of the first and second fibrous layers comprises thermoplastic fibers of a material selected from the group consisting of polypropylene, polyethylene, polyester, polyurethane, nylon and blends thereof.

8. An absorbent article comprising a fluid-pervious topsheet, a fluid-impervious backsheet and an absorbent body disposed therebetween, wherein the improvement comprises as said topsheet a laminated fibrous web according to claim 2.

9. A process for making a laminated fibrous web, comprising the steps of:
    a. forming a first fibrous layer having a first density;
    b. bonding fibers of said first fibrous layer to one another with a first, spaced-apart bonding pattern having a first bonding area;
    c. forming a second fibrous layer having a second density which is less than said first fibrous layer density;
    d. bonding fibers of said second fibrous layer to one another with a second, spaced-apart bonding pattern having a second bonding area which is less than said first pattern bonding area; and
    e. wherein said second bonding pattern produces bonds between said first and second fibrous layers, and said first bonding pattern does not produce bonds between said first and second fibrous layers.

10. A process as recited in claim 9, wherein said forming step (c) comprises the step of depositing fibers onto said first fibrous layer after said first fibrous layer has been bonded with said first bonding pattern.

11. A process as recited in claim 9, wherein said bonding step (b) provides a first series of bonds which extends into said fibrous layer but stops short of an interface between said first and second fibrous layers, and wherein said second bonding step (d) pattern provides a series of bonds which extend entirely through said second fibrous layer to said interface.

12. A process according to claim 9, wherein the third lower extent of bonding is substantially equal to the second lower extent of bonding.

13. A process according to claim 9, wherein the fibers in the second fibrous layer are bonded to one another concurrently with the bonding of the first fibrous layer to the second fibrous layer.

14. A process according to claim 9, wherein the steps of forming and bonding each of the first and second fibrous layers comprises spunbonding of webs as each of said first and second fibrous layers.

15. A process according to claim 9, comprising thermally pattern-bonding the fibers in the first and second fibrous layers to one another in each of such layers and thermally pattern-bonding the first fibrous layer to the second fibrous layer.

16. A process according to claim 9, wherein at least one of the first and second fibrous layers comprises thermoplastic fibers of a material selected from the group consisting of polypropylene, polyethylene, polyester, polyurethane, nylon and blends thereof.

17. An apparatus for forming a laminated fibrous web, comprising:
means for forming a first fibrous layer having a first density, as determined prior to bonding thereof;
first pattern bonding means for bonding fibers of said first fibrous layer to one another with a first, spaced-apart bonding pattern having a first bonding area;
means for forming a second fibrous layer having a second density, which is determined prior to bonding thereof and is less than the density of said first fibrous layer; and
second pattern bonding means for bonding fibers of said second fibrous layer to one another with a second, spaced-apart bonding pattern having a second bonding area which is less than said first pattern bonding area, and for bonding said second fibrous layer to said first fibrous layer.

18. An apparatus as recited in clam 17, wherein said first pattern bonding means provides a first series of bonds which extend into said first fibrous layer but stop short of an interface between said first and second fibrous layers, and wherein said second pattern bonding means provides a second series of bonds which extend through said second fibrous layer to said interface.

19. An apparatus for forming a laminated fibrous web, comprising:
means for forming a first fibrous layer having a first density, as determined prior to bonding thereof;
a first pattern-bonding roll having on its surface an array of protrusions spaced-apart from one another to define a first bonding area constituted by the areal extent of the protrusions;
means for heating the first pattern roll;
means for rotating the first pattern roll;
means for translating the first fibrous layer in contact with the first pattern roll during rotation and heating thereof to form thereon a first bonding pattern;
means for forming a second fibrous layer having a second density, which is determined prior to bonding thereof and is less than the density of said first fibrous layer; and
a second pattern roll having on its surface an array of protrusions spaced-apart from one another to define a second pattern-bonding area measured by the areal extent of the protrusions on the second pattern roll which is less than said first bonding area;
means for rotating the second pattern roll;
means for heating the second pattern roll;
means for mating the first fibrous layer after pattern-bonding thereof by the first pattern roll to the second fibrous layer, with the second fibrous layer overlying said first fibrous layer to form a laminated fibrous web; and
means for translating said laminated fibrous web in contact with the second pattern roll during rotation and heating thereof, and for pattern-bonding of the second fibrous layer such that the fibers of the second fibrous layer are pattern-bonded to one another and so that the second fibrous layer is pattern-bonded to the first fibrous layer;
wherein said second pattern-bonding roll is constructed to form bonds between said first and second fibrous layers, and said first pattern-bonding roll is constructed to form no bonds between said first and second fibrous layers.

20. An apparatus as recited in claim 18 further comprising means for mating said first fibrous layer with said second fibrous layer in an overlying position.

21. Apparatus according to claim 19, wherein the ratio of pattern-bonding area of the second pattern roll to the pattern-bonding area of the first pattern roll is at least about 1:10 but is less than 1:1.

22. An apparatus for forming a laminated fibrous web, comprising:
means for forming a first fibrous layer;
first pattern bonding means for bonding fibers of said first fibrous layer to one another with a first, spaced-apart bonding pattern having a first bonding area;
means for forming a second fibrous layer;
second pattern bonding means for bonding fibers of said second fibrous layer to one another with a second, spaced-apart bonding pattern having a second bonding area which is less than said first bonding area, and for bonding said second fibrous layer to said first fibrous layer,
wherein said first pattern bonding means provides a first series of bonds which extend into said first fibrous layer but stop short of an interface between said first and second fibrous layers, and wherein said second pattern bonding means provides a second series of bonds which extend through only said second fibrous layer to said interface.

* * * * *